United States Patent

Rippstein

[11] Patent Number: 6,143,029
[45] Date of Patent: Nov. 7, 2000

[54] TENDON GUIDE DEVICE

[76] Inventor: Pascal François Rippstein, Forchstrasse 460, CH-8702 Zollikon, Switzerland

[21] Appl. No.: 09/142,554
[22] PCT Filed: Mar. 11, 1997
[86] PCT No.: PCT/CH97/00099
§ 371 Date: Sep. 9, 1998
§ 102(e) Date: Sep. 9, 1998
[87] PCT Pub. No.: WO97/33535
PCT Pub. Date: Sep. 18, 1997

[30] Foreign Application Priority Data

Mar. 11, 1996 [FR] France ................................... 96 03190

[51] Int. Cl.[7] ......................................................... A61F 2/08
[52] U.S. Cl. ........................... 623/13.14; 602/72; 602/36; 623/13.11
[58] Field of Search .................................. 623/13, 11, 66, 623/1, 16, 18, 17; 606/72, 73; 602/36

[56] References Cited

U.S. PATENT DOCUMENTS 5,451,203  9/1995  Lamb ......................................... 602/36
5,456,721  10/1995  Legrad ....................................... 623/13

FOREIGN PATENT DOCUMENTS

| 0 145 492 A2 | 6/1985 | European Pat. Off. . |
| WO 93/09730 | 3/1993 | European Pat. Off. ............ 623/13.14 |
| 0 642 773 A1 | 9/1994 | European Pat. Off. . |
| 2676823 | 1/1993 | France ................................ 623/13.14 |
| WO 96/03084 | 2/1996 | WIPO . |

Primary Examiner—David H. Willse
Assistant Examiner—Suzette J. Jackson
Attorney, Agent, or Firm—Davis and Bujold

[57] ABSTRACT

A tendon guide device comprising a net (1) consisting of a wire mesh made of metal or a synthetic material, for supporting a tendon (10). The device is provided with a malleable tail (7) with a rounded end (9) extending away from the closed end (5) of the net for leading the tendon into a passage in a bone, and an insertion guide (12) enabling the tendon (10) to be inserted into the open end (3) of the net (1). The meshes (2) of the mesh are flexible and thus adjustable between a loosened position in which the tendon (10) is readily insertable by way of the guide (12) and a tightened position in which the tendon may be trapped without using anchoring mechanisms when the two ends of the net (1) are pulled apart.

10 Claims, 2 Drawing Sheets

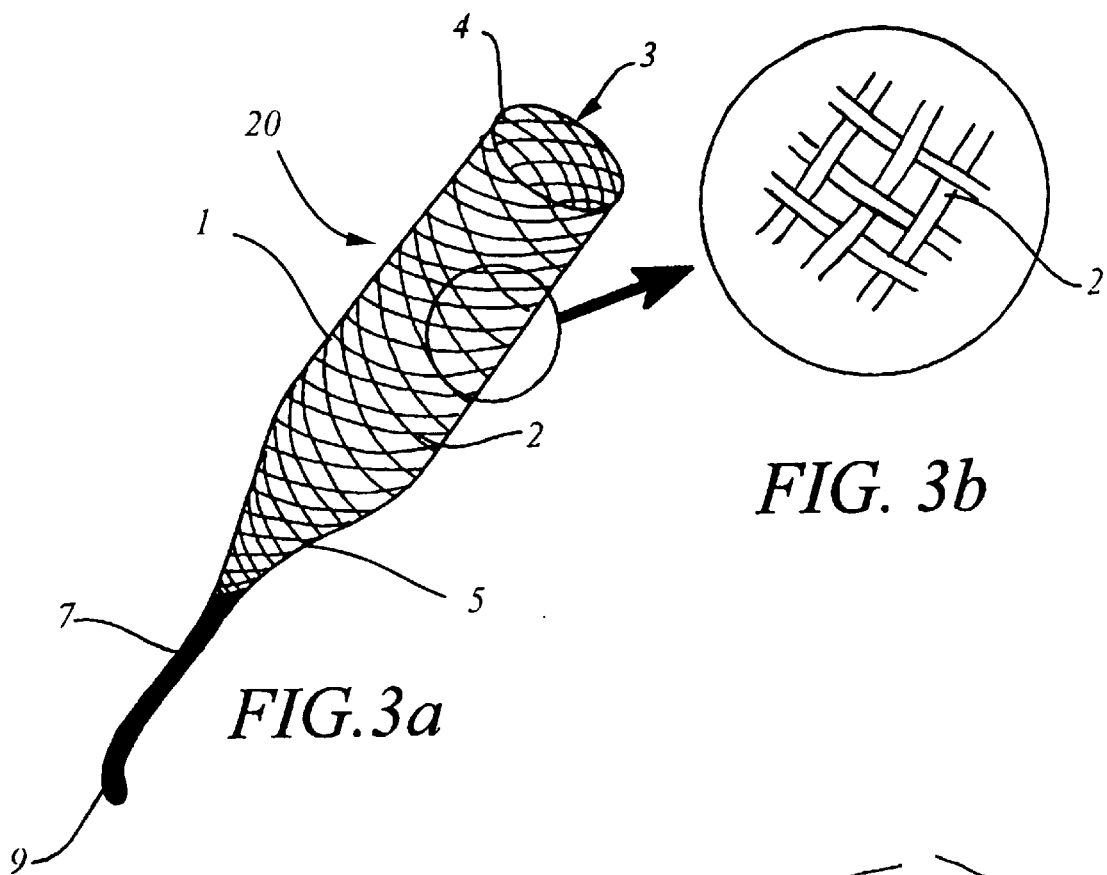
FIG. 3a
FIG. 3b
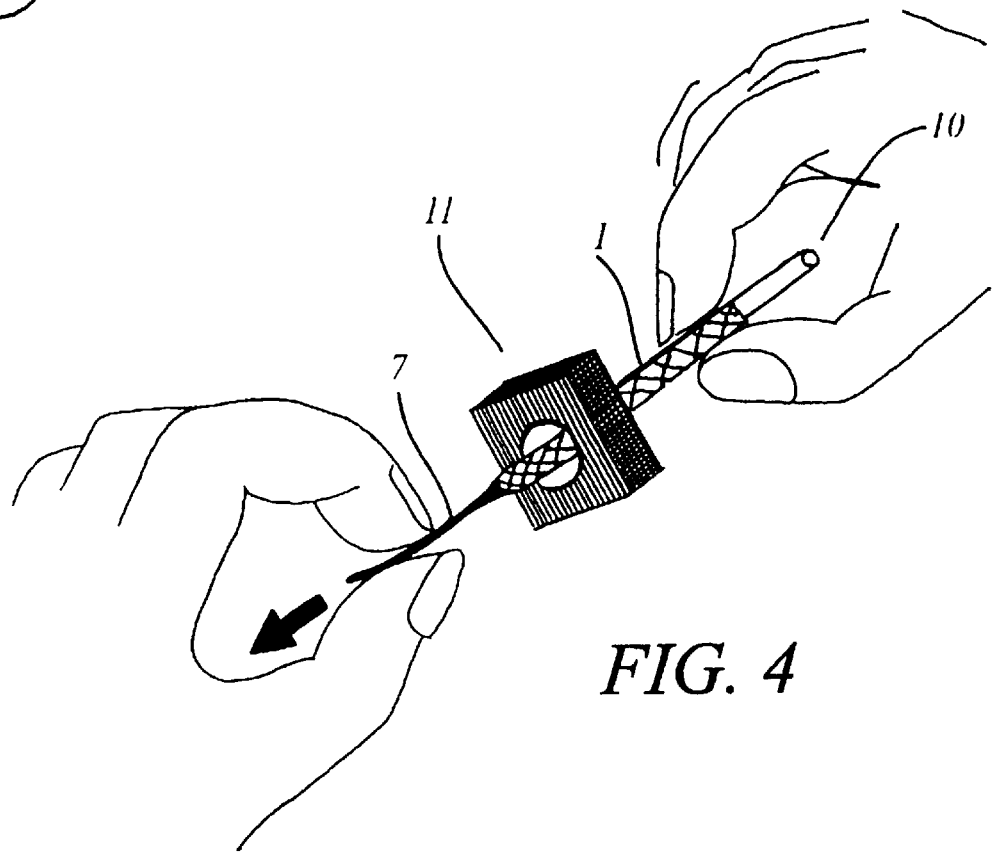
FIG. 4

TENDON GUIDE DEVICE

The present invention concerns a tendon guide device particularly useful in hand and foot surgery, and more specifically, for leading a tendon through an opening in a bone which may be an angled opening.

BACKGROUND OF THE INVENTION

If a ligament is torn in the foot, hand, or joint, the surgical procedure used to prevent permanent impairment consists of either restoring the damaged tendon with surgical elements, as described, for example, in Publication Nos. WO-A-96 03084 and EP-A-O 145 492, or replacing the torn ligament with either a substitute biological tendon as described in Publication No. EP-A-O 642 773, or with an auxiliary tendon of less functional importance which can be removed without harming the patient. To do this, the tendon is guided through passageways in the bone which are generally formed as close as possible to the original location of the torn ligament. The tendon then forms either a single loop, a double loop, a figure eight, or some other shape, and replaces the torn ligament. Moreover, in the majority of musculo-tendon transplants performed for various hand and foot pathologies, the transplanted tendon or tendons are removed from a distal insertion point and reinserted at a new location through a passage in the bone. The tendon is inserted through the tunnel, then usually formed into a knot, and sutured either onto itself or directly onto the periosteum.

The major difficulty in these interventions often consists of inserting the tendon through bone passageways that are hardly much larger than the diameter of the tendon, since there may be only small amount of bone in the area, making it impossible to form a larger tunnel. In addition, in order for the tendon to become quickly and solidly integrated within the bone, it is preferable to establish contact as intimately as possible between the bone and the tendon.

The method known in the art, used conventionally, consists of first using a needle to anchor a thread or wire to the end of the tendon. To ensure a tight attachment, the thread is passed through the tendon several times. Next, the thread and the needle attached to it are passed through the bone passageway and finally, the thread is pulled so the tendon will pass through the bone opening.

This method has numerous disadvantages. First, since the thread must pass through the tendon several times, the tendon can be damaged and weakened. This causes more problems, since the tendon is short and its maximum length should be used. Moreover, the structure of a tendon approximately resembles that of a string composed of several threads, all nearly identical in diameter. Because of this structure, the thread is never very solidly anchored, and it often weakens when pulled hard enough to move the tendon through the bone passageway. If the attachment breaks, tendon damage is worsened, and reattachment is very difficult.

In addition, the tunnel formed in the bone is usually fairly approximate, having been made with a simple boring instrument. Often two V shaped holes are made to form the passageways, resulting in highly variable configurations.

On the other hand, needles have a definite configuration which can be modified only slightly by bending them. If the configuration of the bone passageway and the needle do not conform to each other, as is often the case, the needle will not pass through the opening freely. Threading the needle through the passageway becomes even more difficult because its point tends to hook onto the spongy bone forming the walls of the passageway.

At this stage, the surgeon either tries to reshape the needle so it is identical to the passageway, until the needle finally breaks, or tries to shape the bone canal tunnel so it is identical to the needle, which often causes a fracture that makes the bone passageway useless.

Next, once the needle and thread have passed through the opening, the tendon must be led through it in turn. This step often poses the major problem in the intervention. In practice, the end of the tendon which reaches the tunnel entry often does not completely penetrate the tunnel. Pulling the thread may cause the tendon to "explode," enlarging its diameter. Therefore, it is sometimes definitively impossible to complete passage. Pulling harder ultimately breaks the attachment. In all these situations, the tendon becomes damaged and the only way to reattach the tendon is to remove the damaged portion.

At this stage the surgeon often uses various pointed instruments to attempt to force the tendon extremity into the tunnel opening, while pulling harder and harder. It is often at this point, however, that the attachment fails. Sometimes an attempt is made to enlarge the hole, at the risk of provoking a fracture and rendering the passageway useless, or to reduce the tendon diameter, which weakens its resistance.

This method transforms an initially simple intervention into a long procedure, complicated by the use of ill-suited tools.

An attempt has been made to resolve these problems by using a surgical device consisting of a small cone-shaped sheath made of flexible plastic. The tendon is slid inside and then anchored by filaments encasing it from end to end. Thus, theoretically this device facilitates threading the tendon through the bone tunnel.

However, this technique has several disadvantages. More specifically, since the tendon itself requires considerable space, the increased diameter of the sheath-tendon unit can make passage through the bone impossible. Also, once the sheath has been removed, the resulting contact between the bone and the tendon is not ideal.

Moreover, the tendon must be anchored to the sheath with thread. This damages the tendon and takes time to accomplish. Furthermore, when the tendon is removed, the attachment must be severed, whereas if the tendon is attached directly, the extra step is eliminated.

Finally, this technique requires that different types of sheaths be used to accommodate various tendon sizes. In addition, the sheaths are relatively expensive. They are stitched and sterilized several times, they wear out, and they need to be replaced regularly. This technique is therefore quite costly.

SUMMARY OF THE INVENTION

The present invention proposes a solution to these problems by providing a tendon guide device that is simple and quick to use. It does not affect the integrity of tendon, it is cost effective, and most importantly, it transforms the tendon positioning intervention into a rapid, effective, and reliable procedure.

To accomplish this, the tendon guide device according to the invention is characterized in that it comprises a holder for the tendon which encases one end of it without requiring the tendon to be anchored to the holder, a means for inserting the tendon into the holder, and a means for guiding the enclosed tendon through the bone passageway, said guide means being associated with the holder.

According to a preferred embodiment, the tendon guide comprises a net forming a cylindrical mesh with flexible openings which are adjustable between a slack position, in which the tendon is easily inserted into the guide, and a tightened position, in which the guide tightly encloses the tendon.

Said net is preferably open at the upper end and closed at the other end, which tapers into a progressively narrow area extending into the guide means.

The mesh is made of either synthetic filaments or wire filaments.

Advantageously, the means for inserting said tendon into said holder consists of a guide made of semi-rigid material.

The guide preferably comprises at one end a tongue or a spline serving as a handle, and at the other end, a hollow cylindrical portion with a longitudinal opening to accommodate one end of said tendon.

In a preferred embodiment, said guide means for inserting the tendon through the bone tunnel has a flexible, malleable stern or tail with one unattached, rounded end, said tail being connected to the progressively tapered portion of the net.

The flexible, malleable stem preferably forms one piece with the net and is composed of juxtaposed filaments of the net attached to one another.

To facilitate the procedure, the net may have a lasso-type loop at the upper extremity which surrounds the tendon.

BRIEF DESCRIPTION OF THE DRAWINGS

The advantages of the present invention will be more apparent from the following description of one embodiment, provided as an example, and with reference to the attached drawings, wherein:

FIG. 3 shows only the net with its guide means;

FIG. 3a is an enlarged detail of the net; and

FIG. 4 shows the tendon guide device of the invention introduced inside a model representing a passageway in a bone, with the mesh openings tightened around a tendon.

DESCRIPTION OF THE PREFERRED EMBODIMENTS

Figure 1:
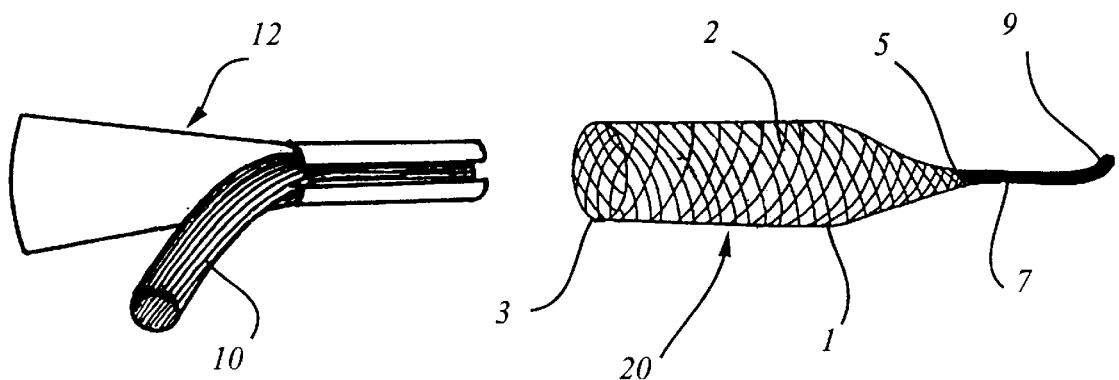
FIG. 1 shows the tendon being positioned inside the net of a tendon guide device according to the invention.

With reference to the drawings, the tendon guide device shown consists first of a holder (20) which encloses a tendon 10 in the form of an elongated, generally cylindrical net 1 made of a network of mesh openings 2, and second, of a means for inserting the tendon into the net 1 in the form of a guide 12.

Figure 2:
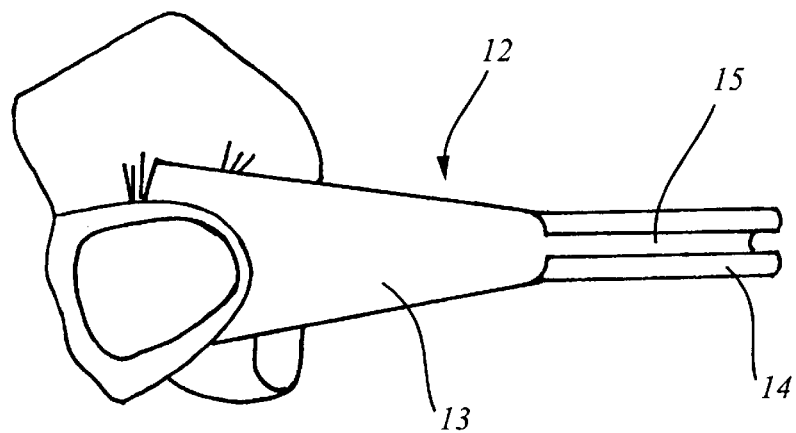
FIG. 2 shows one embodiment of the insertion guide for the device of FIG. 1.

Insertion guide 12, as shown in FIG. 2, is made of a semi-rigid synthetic material with a tongue or spline 13 at one end for a handle and a hollow cylindrical portion 14 at the other end which receives the extremity of the tendon 10. A longitudinal groove 15 runs along the entire length of hollow portion 14 for this purpose. The point of an appropriate instrument is inserted into the groove to force tendon 10 to slide into guide 12. The purpose of the guide is to serve as a tendon "shield" while it is being positioned inside the net, since the tendon is flexible, and also to prevent the tendon from snaring in the mesh openings of the net.

The mesh openings 2 of the network forming net 1 shown in FIGS. 1 and 3 are made of a synthetic material, specifically filaments of Nylon®, Vicryl®, or some other suitable material, or wire. As shown in FIG. 3a, the mesh openings in the net are slack when the device is at rest. The upper extremity 3 of the net is open and it has a larger diameter than the tendon when the net is at rest. The lower extremity 5 of the net is closed and extends into a tail 7 terminating in a rounded end 9. Between tail 7, which defines the lower extremity of the device and serves as a means for guiding the tendon through the bone passageway, and upper extremity 3 of net 1, there is an area which tapers progressively. There is a sort of lasso loop 4 in the last mesh sections of the upper extremity 3 of the net, which is made of only one filament, theoretically the same material as the net.

Tendon 10 is positioned inside the device of the invention in the following manner:

the tendon is placed inside guide 12 by introducing it into the cylindrical portion and sliding it to the end of this portion by inserting the point of an appropriate instrument in groove 15;

the unit formed of guide 12 and tendon 10 is introduced into net 1, with the mesh openings slack;

guide 12 is withdrawn while tendon 10 is held inside the net by the point of an instrument inserted through the mesh openings in the net and through groove 15;

once the tendon has been introduced inside the net, loop 4 is tightened around the tendon and hand tied according to the usual surgical procedure. This allows net 1 to be tightened without requiring that the upper end of it be grasped manually, which is sometimes difficult, depending upon the type of intervention, since the surgical field may be very narrow, the tendon quite small, and so forth. Loop 4 does not damage the tendon. If necessary—for instance, if the size of loop interferes with the tendon's passage because of the knot or because it makes the tendon swell—the loop can be sectioned and removed just prior to passage into the bone opening, since at this point the end of the tendon has already through into the tunnel in the bone and the rest of the tendon will follow with no problems.

Tail 7 is made of flexible, malleable material which can be deformed without losing its original shape. This quality is very useful as it passes through a bone opening which may be sharply angled or complex in shape. The tail may consist of the extended portion of net 1, with the filaments soldered to one another or attached by some other suitable synthetic means. However, it may also be independent of the filaments in the net and joined to the net.

When a surgeon wishes to replace a torn tendon, he sometimes first bores two V-shaped holes to make a passageway through the bone, as in the conventional method described in prior art procedures. The surgeon might also bore only one rectilinear hole or a round opening using a rounded instrument. Next, because it is flexible, tail 7 is preshaped, and it will maintain the shape the surgeon has imparted so as to follow the configuration of the bone passageway. Thus, the surgeon can thread tail 7 through this tunnel very easily.

Next the surgeon "compresses" the device by bringing together upper end 3 of the net and rounded end 9 of tail 7. This causes mesh openings 2 to enlarge and expands the diameter of net 1. The surgeon can now introduce the tendon inside the net with no difficulty, using the procedure already described.

Thereafter, as shown in FIG. 4, the surgeon stretches the device, separating extremities 3 and 9 while pulling tail 7 and keeping open end 3 of net 1 on tendon 10. This causes mesh openings 2 to tighten around tendon 10, decreasing the diameter of the net until it surrounds the tendon securely and traps it. The more the tail is pulled, the more tightly tendon 10 is anchored and secured inside net 1. Finally, the surgeon need only lead the unit of net-tendon 1, 10 through bone passageway 11. This procedure is quite simple to accomplish since the net-tendon unit is perfectly compact. The net surrounding the tendon adds only negligible bulk, particularly in light of the fact that the unit compresses the tendon, making its diameter slightly smaller than usual.

Using the device of the invention, tendon 10 is anchored in net 1 very quickly, securely, and without risk of damage. The device is temporary and eliminates the use of an anchoring thread, which can damage the tendon. In addition, the maneuver can be repeated several times with no adverse effect on the integrity of the tendon if the tendon must be passed through several bone openings or through the same opening several times.

The order of the manipulations performed to introduce tendon 10 inside net 1 can be varied. It is also possible to introduce guide 12 into the net in advance and then insert the tendon inside the guide.

I claim:

1. A tendon guide device for passing a tendon through an opening in a bone which may be an angled opening, comprising a support element (20) for supporting one end of said tendon (10), said element being equipped with a flexible tail (7) for leading the tendon through the bone opening (11), and an insertion guide (12) for inserting said tendon into said support element, wherein the insertion guide (12) comprises at a first end a tongue-like handle (13) and at a second end a hollow cylindrical portion (14) having a longitudinal groove (15) adapted to hold one end of said tendon.

2. The tendon guide device according to claim 1, wherein said insertion guide (12) is made of semirigid synthetic material.

3. The tendon guide device according to claim 1, wherein said tendon support element (20) is generally a cylindrical net (1) with a compressible mesh network (2) adjustable between a slackened position, in which the tendon (10) is easily introduced inside, and a tightened position in which the tendon is tightly enclosed.

4. The tendon guide device according to claim 3, wherein said net (1) is open at an upper end (3) and closed at an opposed end to said upper end by a progressively tapering portion.

5. The tendon guide device according to claim 3, wherein said net is made of filaments of synthetic material.

6. The tendon guide device according to claim 3, wherein said net is made of metal wire.

7. The tendon guide device according to claim 1, wherein said flexible tail (7) is malleable and has a round end (9).

8. The tendon guide device according to claim 4, wherein said flexible tail (7) is connected to said net (1) at the progressively tapering portion and forms one piece with said net.

9. The tendon guide device according to claim 8, wherein said flexible tail (7) is formed of juxtaposed filaments of the net connected to each other.

10. The tendon guide device according to claim 4, wherein said net (1) comprises a lasso-type loop (4) at the upper end (3).

* * * * *